US00PP10264P

United States Patent [19]

Osiecki

[11] Patent Number: Plant 10,264

[45] Date of Patent: Feb. 24, 1998

[54] ANTHURIUM PLANT "A6"

[75] Inventor: Marian W. Osiecki, Marianna, Fla.

[73] Assignee: Oglesby Plant Laboratories, Inc., Altha, Fla.

[21] Appl. No.: 756,937

[22] Filed: Dec. 2, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Rothwell, Figg, Ernst & Kurz

[57] ABSTRACT

A new variety of Anthurium is provided. It is a medium size plant, suitable for production in 15 cm to 25 cm pots from a single tissue culture produced microcutting with vigorous growth; early and abundant branching; early and abundant year-round flowering. Leathery, extremely dark green and glossy leaves sharply contrast with long-lasting, medium, uniform-in-size spathes of unusual pink color with dark spadixes. Most spathes are held almost centrally at nearly the same level above foliage on strong peduncles, red in their distal part.

2 Drawing Sheets

SUMMARY OF THE INVENTION

This invention relates to a new and distinct Anthurium cultivar characterized by the following combination of repeatedly observed traits:

1. Medium size plant of a regular, compact growth habit,
2. vigorous growth,
3. early and abundant branching,
4. leathery, exceptionally dark green and glossy leaves,
5. early, exceptionally abundant and year-round flowering,
6. medium size spathes, relatively uniform in size, held on strong peduncles,
7. majority of spathes held centrally at nearly the same level above foliage,
8. long-lasting spathes of unusual pink color contrasting with dark foliage and dark spadix,
9. peduncles red above foliage contrasting with foliage and spathes and primarily selected for those characteristics being so selected from the progeny of the cross stated below being grown near Altha, Fla. in a cultivated area.

ORIGIN AND ASEXUAL REPRODUCTION

Asexual reproduction of this cultivar by tissue culture was directed by me, such reproduction establishing that the plant does in fact maintain the characteristics described, in successive generations.

The plant was initially selected where grown in a planned breeding program in or near Altha, Fla. and has since been reproduced by plant tissue culture in the vicinity of Altha, Fla. with the characteristics stated. The female parent was a selected clone of Anthurium 'Southern Blush' designated "303" and the male parent was a selected mutant of Anthurium 'Lady Jane' designated "MLJ891". The cross was made in 1991 and the seedling was selected in 1992.

This new cultivar has been identified as Anthurium 'A6'. It is possible that other identification will be adopted in the trade, but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'A6' was approximately 19.5 months from planting a single tissue cultured microcutting and was grown in a 15 cm pot.

In the photographs:

DETAILED DESCRIPTION OF THE NEW CULTIVAR

Figure 1:
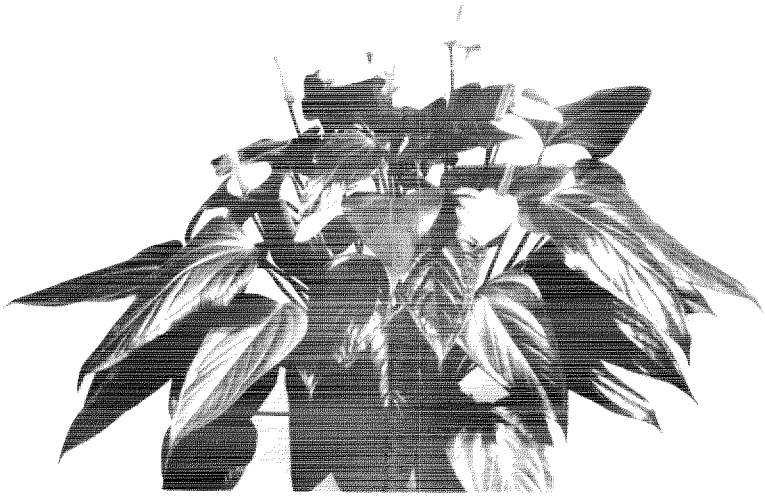
FIG. 1 depicts the whole plant.
Figure 2:
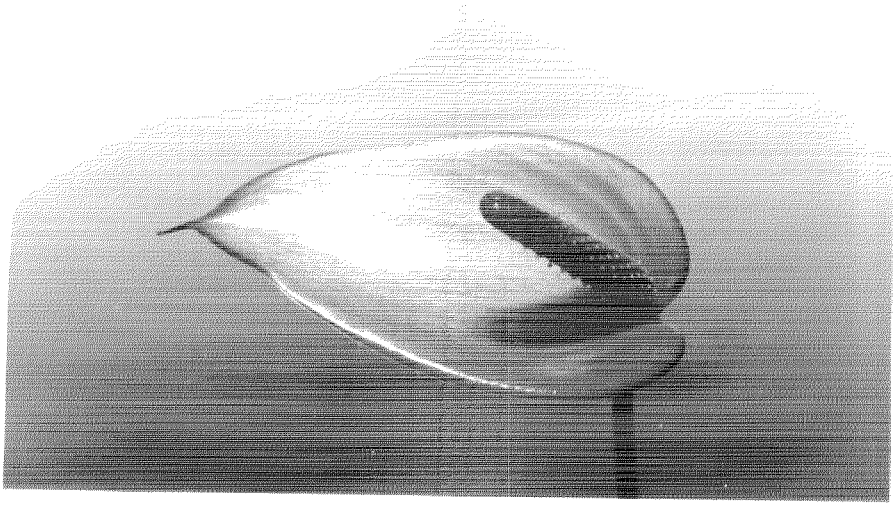
FIG. 2 illustrates the mature inflorescence.
Figure 3:
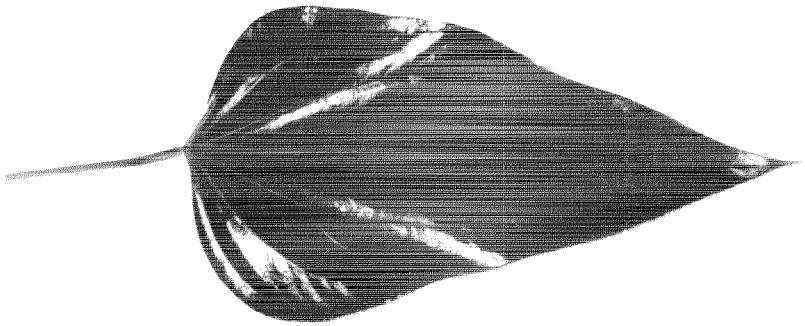
FIG. 3 illustrates a top of a mature leaf.
Figure 4:
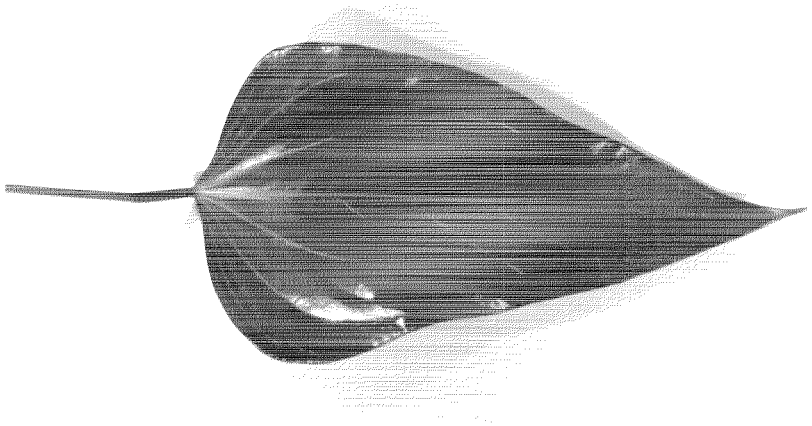
FIG. 4 illustrates the bottom of a mature leaf.

The following observations and measurements describe plants grown near Altha, Fla. under greenhouse conditions. These observations and measurements were recorded in January and February, 1996 from mature plants (about 18 months from planting tissue cultured microcuttings) grown in 15 cm pots. Fully developed organs were used for measurements and color description, unless otherwise indicated. Color values were determined under natural, indirect light of approximately 300–850 foot-candles. Color references are made to The R.H.S. Color Chart, except where general color terms of ordinary significance are used.

'A6' has not been observed under all possible environmental conditions. The phenotype may vary with variations in environment and horticultural practices, such as temperature, light intensity, day length, fertilization and propagation procedure, without any change in genotype.

PARENTAGE:

*Female parent.*—Anthurium 'Southern Blush' designated "303".

*Male parent.*—Anthurium 'Lady Jane' MLJ designated "891".

Propagation: Plant tissue culture.

Plant descriptions:

*Growth habit.*—Medium size, compact, with short stems, well branched, main stem not distinct.

*Height.*—Foliage 32–41 cm; with spathes 36–46 cm.

*Width.*—74–81 cm.

Petiole:

*Size.*—26.0–31.5 cm long, 3.9–4.6 mm in diameter at the mid length; cross section almost round at the mid length.

*Geniculum.*—3.0–3.3 cm long, 4.3–4.9 mm in diameter at the base, not very prominent; usually a small knob is situated on each side of the shallow central groove, immediately below base of the leaf blade; sometimes petiole slightly bends at the base of geniculum.

*Petiole wings.*—1.8–2.5 cm long, not conspicuous.

*Color.*—Geniculum: Adaxial: 200A–C (brown), usually with some lighter color close to the juncture with leaf blade. Abaxial: Similar to 152A, sometimes with some resemblance to 146A (both yellow-green). Below Geniculum: Adaxial: Mixture of brown (200B–C) and yellow-green (146A, 148A); in the distal half brown color dominates; with increasing distance from geniculum ratio of green to brown generally increases, except immediately below geniculum, where sometimes there is a little more green than in the zone below it. The area near wings tips is similar to, but darker than 146A (yellow green). Abaxial: Immediately below geniculum — between 144A and 146B (both yellow-green); it merges with the color similar to 146A–B at the mid length and a color darker than 146A at the base. Petiole wings: Similar to 146A (yellow-green).

Leaf blade:

*Position.*Most leaf blades are approximately horizontal or point slightly downwards.

*Shape.*—Ovate, slightly asymmetric; tip acuminate, long, usually slightly curved; base truncate, often slightly asymmetric. Leaves produced at early stage of plant development have more obtuse bases. Blade is usually almost flat.

*Size.*—21.5–24.5 cm long; 11.6–14.5 cm wide; length to width ratio 1.7–1.9:1.

*Texture.*—Thick, leathery, smooth, glossy; young leaves highly polished.

*Veins.*—Prominent near the base, less conspicuous near the tip. Proximal more than ½ but less than ⅔ of the midrib protrudes from the adaxial surface; distal portions are somewhat sunken. Well defined primary veins (usually 6) radiate out from the juncture of the leaf blade and the petiole. The two primary veins adjacent to each side of the midrib protrude from the adaxial surface near the base. The outermost primary veins are entirely sunken. Midrib and all primary veins protrude from the abaxial leaf blade surface.

*Color.*—Newly unrolled, not expanded leaf: A fine dark greyed-purple line (fraction of a mm in width) present along edges on both sides; more pronounced on the abaxial side. Adaxial: 146A (yellow-green) immediately around petiole juncture (approximately 5–7 mm radius); darker with increasing distance from the juncture. Most of the leaf blade is darker than 147A (yellow-green), with some purple-brown tint on very young leaves; veins: near base — midrib and primary veins lighter than the surrounding tissue; near tip — midrib similar to or more purple-brown than surrounding tissue (similar to the edge). Abaxial: More uniform in color than the adaxial surface; 146A (yellow-green) at the petiole juncture; darker with increasing distance, merges with a color darker than 148A (yellow green); veins: near base — midrib and primary veins a little lighter than the surrounding tissue; distal half — midrib and primary veins darker or similar to the surrounding tissue. Mature Leaf: Adaxial Much darker than 147A (yellow-green); veins: 200C (brown) adjacent to petiole. With increasing distance from the petiole brown color narrows to center of veins and eventually disappears; bordering the narrowing brown line and distal to its disappearance, veins are lighter than the surrounding tissue; in the distal half all veins approximate surrounding tissue in color. Abaxial: 146B, sometimes with some resemblance to 147B (both yellow-green); veins: almost entire midrib and proximal approximately ⅓ to ½ of primary veins 144A–B (yellow-green); often primary veins, especially more distant from the midrib and occasionally the midrib show some brown or red-brown coloration near petiole.

Scale leaf covering lateral vegetative bud (opposite to the mature inflorescence):

*Length.*—9.3–11.5 cm.

*Color.*—Abaxial 144A–B (yellow-green), somewhat translucent; in some areas this color mixed or replaced by greyed-red colors; central area of the base — one or more of the following greyed-red colors: 180C–D, 181C–D, 179B; center of the proximal half above base — a darker greyed-red color mixed with yellow-green; sides of the proximal half yellow-green (144A–B). In the distal half the pronounced central rib is greyed-red, darker than the adjacent areas, which are a mixture of greyed-red and yellow-green; edges in the distal half similar in color to the center of the base. Adaxial: Colors similar to the ones found on the abaxial side; longitudinal greyed-red (182C–D, 181C–D) band in the center tapers and becomes darker toward the tip; in the basal ⅓ the areas on both sides of the central band are yellow-green (144A–B); with the increasing distance from base the amount of greyed-red increases; in the distal half color of the edges is similar to that of central band, intervening areas are a mixture of yellow-green and greyed-red.

Scale leaf between peduncle of a young inflorescence and the stem:

*Length.*—3.7–4.5 cm.

*Color.*—Abaxial: 145B–C, 144C–D (both yellow-green), a little translucent; thin dotted brown line on the edge of two longitudinal elevated ribs; tip and areas around bases of the ribs dark pink to greyed-red. Scale leaf fades and dries shortly after spathe matures.

Inflorescence:

*Arrangement.*—Usually numerous spathes of relatively uniform size carried centrally at about the same level above foliage on straight peduncles. Spadix situated low on the spathe. Ratio spathe length to spadix length 1.5–1.7:1. Front side distance between a juncture of peduncle and spathe base and the lowermost flowers on the spadix 6.5–9.0 mm.

*Development.*—Before opening buds oblique with tips pointing upwards at various angles or horizontal. Distal end of spathe unrolls first, exposing tip of spadix before its base. In a newly opened inflorescence spadix and spathe are usually almost parallel and leaning backwards; when spathe opens pistils are visible on basal approximately 50% of spadix, with small indentations (pistil imprints) often visible on the front spathe surface; within several hours to two days spathe fully opens and becomes reflexed while spadix starts moving towards the vertical position. At maturity spadix is vertical or slightly leans backwards and spathe is almost horizontal with tip curving backwards.

Peduncle:

*Size.*—28.8–37.8 cm long; 3.1–4.3 mm in diameter at the mid length; cross section approximately round at the mid length.

*Stipe.*—Very short (not measurable).

*Color.*—Front: between spathe and base of spadix 45A (red); immediately below spathe to approximately 2.0–2.5 cm — 185A, often with some 184A (both greyed-purple); sometimes narrow central longitudinal stripe more red than the adjacent areas; proximally colors become gradations of greyed-red, greyed-orange and brown (178A, 183B–A, 176A, 166A, 165A or darker and a color between 200C and 200D). From the mid length proximally increasing amounts of yellow-green appear (beginning with 152A and lower 146A), mixed with one or a few of the above mentioned brown and greyed-red/orange colors and/or a color darker than 199A (grey-brown). Color of the proximal half greatly depends on the extent to which a peduncle is exposed to light. Shielded peduncles are more yellow-green than those more exposed, which are darker and more brown; base is always yellow-green (146A). Back: Immediately below spathe to approximately 2.0–2.5 cm — 46A (red) or a little lighter. Below red zone colors of greyed-red group are present (181A or darker, 180A or darker, 183B or lighter, 178A–B, 176A). At the mid length color is darker and more brown than 152A (yellow-green). Brown (200D) and greyed-orange (165A and 166A) colors are present nearer the base.

Spathe:

*Shape.*—Ovate, at maturity almost flat with lobes slightly curving forwards from the juncture with peduncle and tip curving backwards; edges slightly curve backwards (except for the tip); tip — between acuminate and aristate, long, with the edges rolling frontwards; base — obtuse, often slightly asymmetric; lobes slightly extend past peduncle.

*Size (flattened).*7.8–10.0 cm long, 4.0–5.8 cm wide; length to width ratio 1.8–2.0:1.

*Texture.*—Smooth, leathery, glossy, highly polished when young.

*Color.*—Closed bud: Similar to and sometimes lighter than 51B, but usually darker than 51C (red).

*Mature spathe (pistils visible on entire spadix length).*—Front: Up to 1 mm wide stripe along the edge 53B (red), except near peduncle, where it becomes greyed-purple (187B). The color of the spathe is not uniform. The darkest area (53B) is adjacent to peduncle; spathe becomes lighter radially and especially towards the tip; lighter areas merge with the darker ones in an irregular fashion, sometimes forming irregular longitudinal bands. In the proximal ⅓ to ½ shades of and between: 53C, 51A–B, 48A, 47D (all red) dominate; in the distal ⅓ the last mentioned colors are dominated by the lighter colors: 51C–D, 50C and a shade lighter than 47D (all red). Veins are darker (approximately 53C) than the surrounding tissue, but less conspicuous than the edge stripe. Back: Edge stripe color is similar to that on the front; the rest of spathe lighter than the front side, composed of irregularly distributed colors 51C–D (red). Veins darker than the surrounding tissue, midrib especially pronounced — approximately 53C (red).

*Newly unrolled spathe.*—Front: Color of the edge is almost the same as at maturity and the remaining area is darker than at maturity; dark red (53B and a shade lighter than 53B) area adjacent to peduncle is greater than at maturity; the other colors in the proximal half are: similar to 51A–B, lighter than 50B, darker than 47D (all red); the distal half is slightly lighter than the proximal part, most similar to 51B or to a color darker than 47D (both red); veins are darker than the remainder of the spathe (approximately 53B). Back: Slightly lighter than the front (51B–C-red), except the edge almost the same as on the front side. Veins darker than the surrounding tissue with the midrib being most prominent (approximately 53B-red).

Spadix:

*Shape.*—Columnar, slightly tapering towards tip.

*Size.*—4.6–5.8 cm long, 5.6–8.0 mm in diameter (with the pistils).

*Color.*—Young inflorescence (pistils visible on proximal approximately ½ of spadix): Proximal half: darker and more purple than 183D (greyed-purple), darker and more grey than 59A (red-purple), lighter than 187A (greyed-purple). Distal half: 59A (red-purple) or 187C (greyed-purple), becomes gradually lighter towards tip. Tip: 185B (greyed-purple). Mature inflorescence (pistils visible on entire spadix length): Lighter and more gray than 59A (red-purple), darker and more purple than 183D (greyed-purple); tip: 59A.

Botanical flower:

*Perianth.*—Prominent between pistils, determines the color of the spadix, segments united.

*Pistil.*—Visible on approximately half of spadix length immediately after spathe opening, at maturity distinctly lighter than perianth; stigmas well visible, fairly large.

*Stamens.*—Not visible before pollen release.

Flowering: Flowers naturally in 15 cm pots, about 9–11 months from planting tissue cultured microcuttings. Continuous year-round flowering. Approximately 18 months after planting tissue cultured microcuttings even to ten spathes visible above or among leaves.

Spathe longevity: Spathe retains pink color for approximately 8–10 weeks following appearance of bud above or among foliage.

Roots: Roots above soil level — few, short, low on the stem, thick, fleshy, non-branching; usually not covered by the scale leaf from beginning of development; young aerial roots — red (47A, 53A–B, 46A, 45A), root cap — yellow with the green tint, tip — green; old aerial roots — gray. Very strong root system below soil level; numerous primary roots, thick, fleshy; rot — hair zone and elongation zone show one or a mixture of the following red colors: 51B–D, 50C, 48A–C, 47C–D; root cap dark yellow; older parts cream in color.

Disease and insect resistance: No unusual susceptibility to diseases or insects noted to date.

COMPARISON WITH THE KNOWN CULTIVARS

The new cultivar can be compared to the known cultivar 'Ruth Morat' U.S. Plant Pat. No. 8,540 a/k/a Lady Ruth. The comparisons were made on plants grown under similar conditions in a greenhouse near Altha, Fla.

'A6' is distinguished from 'Ruth Morat' by its more regular and more compact growth habit; darker, more glossy and smaller leaf blades; earlier and more abundant flowering; narrower, pink spathes, darker spadix; darker peduncles and petioles; majority of opened spathes situated at about the same level above the foliage, centrally located on the plant and by the occurrence of red in the roots.

I claim:

1. A new and distinct cultivar of Anthurium plant named 'A6', substantially as described and illustrated herein, characterized particularly as to novelty by its medium size; regular and compact growth habit; vigorous growth; early and abundant branching; exceptionally dark, glossy foliage; early and exceptionally abundant year-round flowering; long-lasting spathes of an unusual pink color carried on straight, strong, distally red peduncles at nearly the same level above foliage and by red-purple spadixes.

* * * * *